(12) United States Patent
Calafiore et al.

(10) Patent No.: US 9,839,615 B2
(45) Date of Patent: Dec. 12, 2017

(54) CLINICAL GRADE SODIUM ALGINATE FOR MICROENCAPSULATION OF MYOFIBROBLASTS ISOLATED FROM WHARTON JELLY FOR PREVENTION AND TREATMENT OF AUTOIMMUNE AND INFLAMMATORY DISEASES

(71) Applicant: Gary Harlem, Dix Hills, NY (US)

(72) Inventors: Riccardo Calafiore, Perugia (IT); Giuseppe Pietro Pio Basta, Perugia (IT); Pia Montanucci, Bastia Umbra (IT)

(73) Assignee: Gary Harlem, Dix Hills, NY (US)

( * ) Notice: Subject to any disclaimer, the term of this patent is extended or adjusted under 35 U.S.C. 154(b) by 0 days.

(21) Appl. No.: 14/680,850

(22) Filed: Apr. 7, 2015

(65) Prior Publication Data

US 2015/0290141 A1    Oct. 15, 2015

Related U.S. Application Data

(60) Provisional application No. 61/978,559, filed on Apr. 11, 2014.

(51) Int. Cl.
*A61K 9/50* (2006.01)
*A61K 35/51* (2015.01)
*A61K 35/34* (2015.01)

(52) U.S. Cl.
CPC .......... *A61K 9/5036* (2013.01); *A61K 9/5031* (2013.01); *A61K 9/5089* (2013.01); *A61K 35/34* (2013.01); *A61K 35/51* (2013.01)

(58) Field of Classification Search
None
See application file for complete search history.

(56) References Cited

U.S. PATENT DOCUMENTS

2010/0226976 A1* 9/2010 Machluf ............. C12N 5/0663 424/451
2011/0250280 A1* 10/2011 Calafiore ............. A61K 9/5036 424/490

OTHER PUBLICATIONS

Ben-Ami et al, Autoimmunity Reviews, 2011, vol. 10, pp. 410-415.*
Liu et al, Arthritis Research and Therapy, 2010, vol. 12: R210 (13 pages).*
Penalozzi et al, Tissue Engineering: Part C, 2010, vol. 15, No. 1, pp. 141-155.*
Trouche et al, Cell Transplantation, 2010, vol. 19, pp. 1623-1633.*
Darrabie et al, "Characteristics of Poly-L-Ornithine-coated alginate microcapsules" Biomaterials, 2005, vol. 26, pp. 6846-6852.*
Sun, A. et al., "Injectable Microencapsulated Islet Cells as a Bioartificial Pancreas," Applied Biochemistry and Biotechnology, Nov. 1983, pp. 87-99, vol. 10.
Montanucci, P. et al., "New Simple and Rapid Method for Purification of Mesenchymal Stem Cells from the Human Umbilical Cord Wharton Jelly," Tissue Engineering: Part A, Aug. 2011, vol. 17, Nos. 21 and 22, pp. 2651-2661.
Montanucci, P. et al.,"In Vitro—Cultured Human Islet Cell Monolayers: Sternness Markers and Insulin Recovery upon Streptozotocin Exposure," Tissue Engineering: Part A, Jul. 2009, pp. 3931-3942, vol. 15, No. 12.

* cited by examiner

*Primary Examiner* — Allison Fox
(74) *Attorney, Agent, or Firm* — Tutunjian & Bitetto, P.C.

(57) ABSTRACT

A method for microencapsulation includes isolating myofibroblasts from Wharton's jelly of a human umbilical cord. The myofibroblasts are microencapsulated using ultra-purified sodium alginate, wherein the myofibroblasts encapsulated in the sodium alginate form a three-dimensional spherical structure.

10 Claims, 8 Drawing Sheets

FIG. 4A
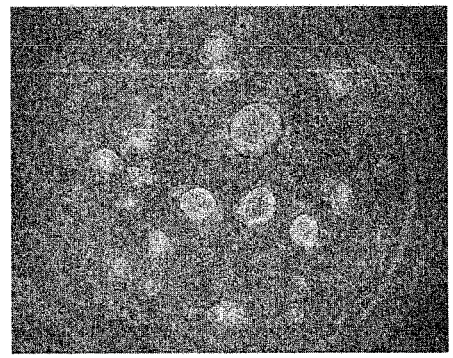
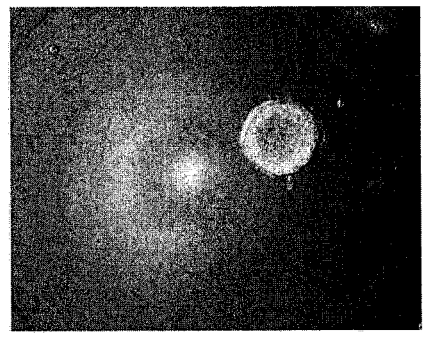
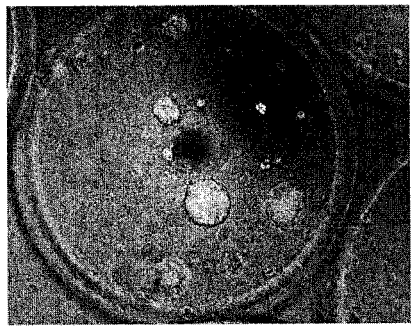
FIG. 4B        FIG. 4C

CLINICAL GRADE SODIUM ALGINATE FOR MICROENCAPSULATION OF MYOFIBROBLASTS ISOLATED FROM WHARTON JELLY FOR PREVENTION AND TREATMENT OF AUTOIMMUNE AND INFLAMMATORY DISEASES

CROSS-REFERENCE TO RELATED APPLICATION

This application claims the benefit of U.S. Provisional Application No. 61/978,559, filed Apr. 11, 2014, the disclosure of which is incorporated herein by reference in its entirety.

BACKGROUND OF THE INVENTION

Technical Field

The present invention generally relates to microencapsulating of myofibroblasts (e.g., isolated from Wharton's jelly of the human umbilical cord) in "clinical grade" sodium alginate for the prevention and therapeutic treatment of autoimmune and inflammatory diseases.

Description of State of the Art

Sodium alginate (AG) is a polysaccharide extracted from seaweed, and in particular, Microcystis pyrifera, present mainly along the western shores of the Pacific Ocean, has a wide application in various industries (i.e., food chain, pharma) including biotechnology. Sodium alginate can be found in the market as a crude extract alginate or as a partially purified powder. Commonly, the KELTONE™ LVCR possesses a level of endotoxin in a range that goes from 30,000 EU/g to about 60,000 EU/g. "Pharmaceutical grade" alginate for parenteral applications must contain endotoxin levels lower than 100 EU/g. Hence, before clinical use KELTONE™ LVCR endotoxin levels must be drastically reduced.

SUMMARY OF THE INVENTION

A method for microencapsulation includes isolating myofibroblasts from Wharton's jelly of a human umbilical cord. The myofibroblasts are microencapsulated using ultra-purified sodium alginate, wherein the myofibroblasts in sodium alginate form a three-dimensional spherical structure. A pharmaceutical product made in accordance with this method is also included.

A pharmaceutical product includes myofibroblasts and a sodium alginate encapsulation material configured to encapsulate the myofibroblasts.

A system for microencapsulation of myofibroblasts includes means for isolating myofibroblasts from Wharton's jelly of a human umbilical cord; and means for microencapsulating the myofibroblasts using ultra-purified sodium alginate, wherein the myofibroblasts in sodium alginate form a three-dimensional spherical structure.

In one aspect of the present principles, a method for the microencapsulation of cells is provided, comprising the steps of isolating myofibroblasts from Wharton's jelly of a human umbilical cord; and microencapsulating the myofibroblasts using a solution of ultra-purified sodium alginate to form microcapsules comprising myofibroblasts encapsulated within sodium alginate, wherein the myofibroblasts encapsulated within the sodium alginate form a three-dimensional spherical structure.

According to another aspect of the present principles, a pharmaceutical product is provided comprising myofibroblasts; and an ultra-purified sodium alginate encapsulation material configured to encapsulate the myofibroblasts.

According to yet another aspect of the present principles, a system for microencapsulation of myofibroblasts is provided comprising means for isolating myofibroblasts from Wharton's jelly of a human umbilical cord; and means for microencapsulating the myofibroblasts to form encapsulated myofibroblasts using ultra-purified sodium alginate, wherein the myofibroblasts in sodium alginate form a three-dimensional spherical structure.

These and other aspects, features and advantages of the present invention will be described or become apparent from the following detailed description of the preferred embodiments, which is to be read in connection with the accompanying drawings.

BRIEF DESCRIPTION OF THE DRAWINGS

The teachings of the present invention can be readily understood by considering the following detailed description in conjunction with the accompanying drawings, in which:

FIG. 3B shows exemplary myofibroblasts microencapsulated in sodium alginate with staining of the cells with ethidium bromide and fluorescein diacetate for the estimation of the vitality;

FIGS. 4A, 4B and 4C depict exemplary myofibroblasts after 16 hours of a procedure of microencapsulation according to an aspect of the present principles, showing a compact 3D architecture;

Figure 1:
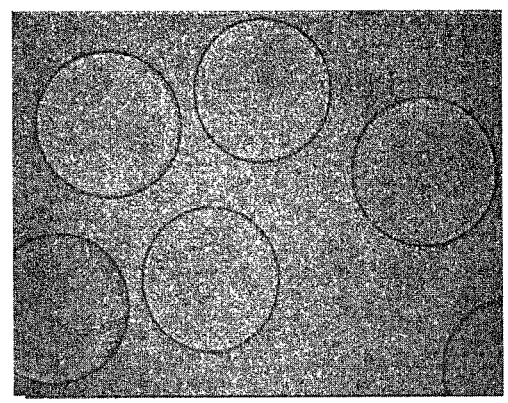
FIG. 1 is an image showing exemplary empty AG microcapsules.

It should be understood that the drawings are for purposes of illustrating the concepts of the invention and are not necessarily the only possible configuration for illustrating the invention.

While multiple embodiments are disclosed, still other embodiments of the present disclosure will become apparent to those skilled in the art from the following detailed description, which is to be read in connection with the accompanying drawing(s). As will be apparent, the disclosure is capable of modifications in various obvious aspects, all without departing from the spirit and scope of the present disclosure. Accordingly, the detailed description is to be regarded as illustrative in nature and not restrictive.

DETAILED DESCRIPTION OF PREFERRED EMBODIMENTS

The present principles provide systems, materials and methods for making and delivering microencapsulated myofibroblasts. Embodiments according to aspects of the present invention cover processes of microencapsulating myofibroblasts (e.g., isolated from Wharton's jelly of the human umbilical cord) in "clinical grade" sodium alginate for the prevention and therapy of autoimmune and inflammatory diseases.

The present principles also relate to a process of encapsulating, with microcapsules that preferably have a spherical shape and a diameter between 400-600 microns. Advantageously, important resultant features of this process include the homogeneity of the final product and absence of empty capsules.

Furthermore, the present principles describe how, after the process of microencapsulation by procedures according to the present invention, the microencapsulated myofibroblasts, extracted from the human umbilical cord Wharton Jelly post-partum, are induced to aggregate and to assume a spherical three-dimensional structure in the absence of single cells. Such 3-D architecture is originally driven by the ultrapurified alginate for making the microcapsules (as produced as described in U.S. patent application Ser. No. 12/863,912, filed on Jul. 21, 2010, the disclosure of which is incorporated herein by reference in its entirety and referred to hereinafter as the "Alginate disclosure").

A product according to the present principles, enables mitigation of the autoimmune and/or inflammatory chronic disease process shared by several disorders that have in common specific gene haplotypes (i.e., DR, DQ etc.). Advantageously, this immunomodulatory action may result in repair/regeneration of the cell/tissue damaged by the inflammatory/immune attack. It is noted that a product according to the present principles including microencapsulated myofibroblasts may coincide with a drug delivery system.

Methods, systems and devices as described herein may be used in the fabrication of microcapsules for use in any part of the body, for pharmaceutical use, for drug delivery, for cell delivery or combinations thereof. The resulting material may be delivered during surgery or for treatment of a living organism or may be employed for testing or growth of cells outside of an organism (e.g., in a Petri dish or the like). The devices/materials may be integrated with or encapsulate other materials in addition to those mentioned herein.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Purified AG has been employed for the preparation of microcapsules containing pancreatic islets for transplantation purposes. In fact, the AG microcapsules AG, "ad hoc" coated with polycations, such as polyornithine, uniquely devised in our laboratory, represent one of the most important methods currently known to protect cell transplants from the host immune response. After 20 years of work, well documented by publications recognized by the international scientific community, the present inventors have developed an advanced AG capsule prototype for grafting human or other islet types, in type 1 diabetic patients or other high mammalians.

While initially, our lab worked with partially purified AG, with endotoxin levels still exceeding 100 EU/g, we then aimed at reaching the "bioinvisibility" criterion, as recommended by US Food and Drug Administration (FDA): this would imply that the endotoxin contaminating levels would be below 100 EU/g. We accomplished this goal by developing ultrapure "clinical grade" AG ("Alginate disclosure") to prepare our microcapsules that were employed in our pilot clinical trials in diabetic patients.

In detail, starting from the powder of AG type "pharmaceutical grade," after molar dilution and multiple filtrations we obtain a final product whose endotoxin content is less than 20 EU/g, in full compliance with the criteria for "quality control" (bioinvisibility) set out above. Our final product, usually available in solution 1.8% (w/v), appropriately stored protected from light and at a temperature of 4°-6° C. is very stable over time, with a protein content which is virtually absent (<0.4%—bioinvisibility criterion of the U.S. FDA). The content of heavy metals is well below the limits.

The alginate powder was purchased from Monsanto Kelco™ and has a molecular weight of between 120000 and 190000 kDa and has the following composition in mannuronic acid (M) and guluronic acid (G): Fraction M (FM), 61%; Fraction G (FG) 39%; therefore it can be called a High M. After ultra-purification, characteristics of the product are shown below in Table 1:

TABLE 1

| Ca: | <100 ppm | Mg: | <40 ppm | Mn: | <10 ppm |
|---|---|---|---|---|---|
| Cu: | <40 ppm | Zn: | <40 ppm | Sr: | <40 ppm |
| Fe: | <60 ppm | Pb: | <50 ppm | As: | <100 ppb |
| Hg: | <40 ppb | Si: | <10 ppm | | |

La viscosità è compresa fra 100-300 cps (Brookfield 25° C., velocità 60 rpm)
pH: 6.6-7.8 (4-25° C.)
Contenuto proteico: <0.45%.
Endotoxin level (measured by LAL test at University of Perugia): <0.5 EU/ml che corrisponde a <27 EU/g [NB. Tutte le soluzioni contenti livelli di endotossine <100 EU/g sono considerate "endotoxin-free"]
"Tabella 1"

Note that other characteristics outside these ranges may be employed.

Microencapsulation Procedure:

The process of microencapsulation of cells of different origin dates back to the early 1980's. See, e.g., "*Injectable microencapsulated islet cells as a bioartificial pancreas.*" Sun A M, O'Shea G M, Goosen M F. Appl Biochem Biotechnol. 1984; 10:87-99. Over the last twenty years, numerous studies have been performed in which the whole-cell microcapsule was proposed as a therapy for various diseases predominantly in immune genesis. In all these studies, attention has been focused to obtain a product that could be applicable to the patient. Our laboratory has been working on biotechnology applications for 25 years. This ultimately allowed us to get permission from the Italian National Health Institute to begin human transplants with microencapsulated human islets (CTR ISRCTN43557935).

FIG. 1 depicts an exemplary image showing empty sodium alginate (AG) microcapsules.

The microencapsulation process used in the present disclosure focuses on how the final de-gelling process, near the end of the procedure, enables the cells' aggregation.

Figure 8:
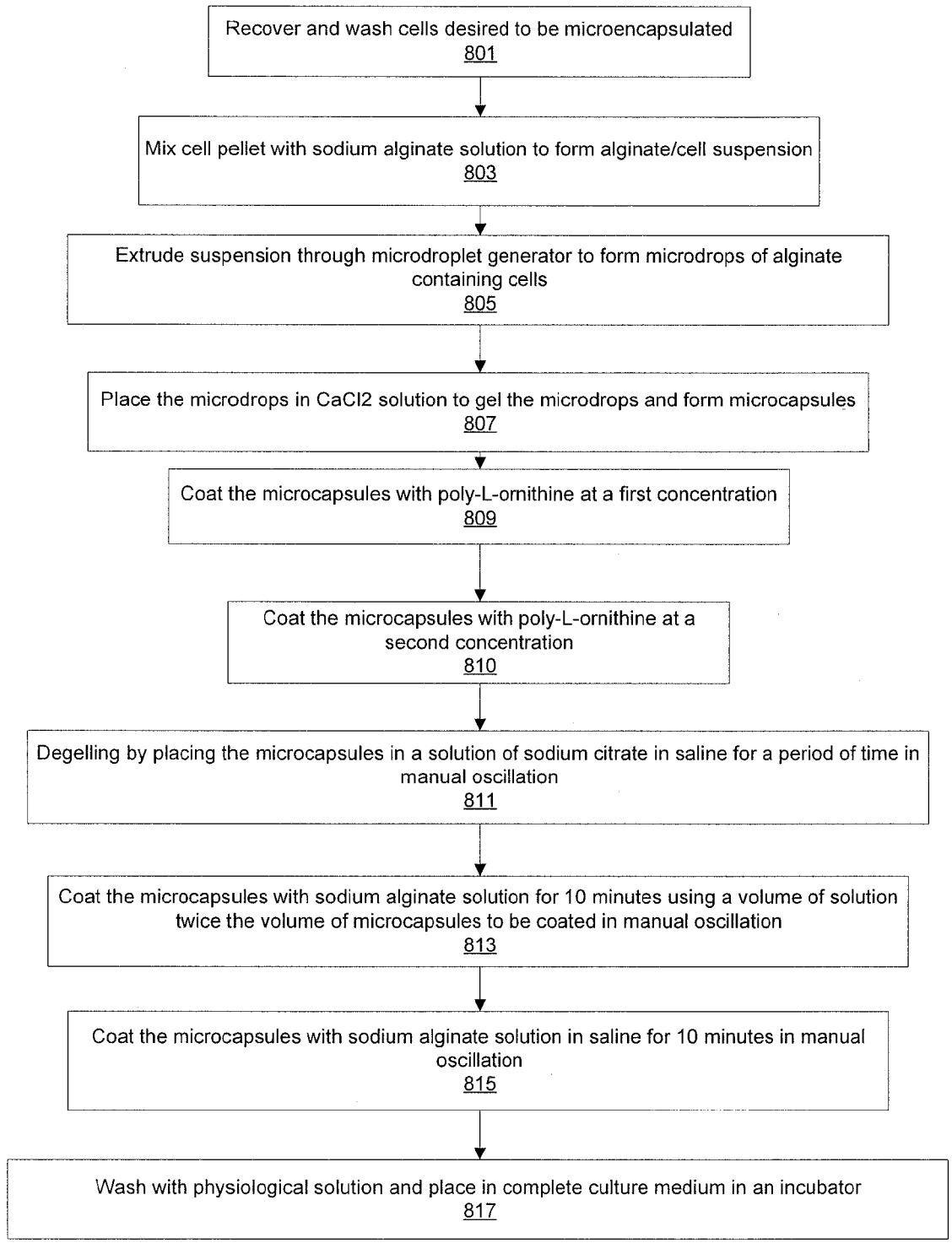
FIG. 8 depicts an exemplary flowchart of a method of microencapsulating cells using sodium alginate according to an aspect of the present principles.

Detailed Procedure:

FIG. 8 depicts an exemplary flowchart of a method of microencapsulating cells using sodium alginate according to an aspect of the present principles. To proceed with microencapsulation, it is necessary to recover the cells (step 801) from the culture flasks, which can be done by standard operating procedure. For example, it is possible to recover the cells using, e.g., trypsin 0.05% for 3 minutes and then blocking the reaction by addition of culture medium containing serum. The cells in suspension are thoroughly washed in saline and then counted.

A microencapsulation procedure according to the present principles includes mixing the cell pellet carefully with a solution of sodium alginate, e.g., 1.8% (step 803) in order to obtain a homogeneous mixture. The alginate/cell suspension preferably includes, e.g., 1.2 ml of 1.8% AG per $1-2 \times 10^6$ cells. We have found that staying with this exact AG/cells ratio allows us to avoid an excessive number of empty capsules or overfilling of the capsules with cells, which can cause subsequent cell protrusion through the capsular wall.

The suspension can be extruded (step 805) through a microdroplet generator 901 [see, e.g., Montanucci P, Basta G, Calafiore R., *In vitro cultured human islet cell monolayers: sternness markers and insulin recovery upon streptozotocin exposure*. Tissue Eng. Part A 2009; 15:3931 e42, the disclosure of which is incorporated herein by reference], using a combination of airflow and mechanical pressure that determines the division of the cell suspension in microdrops.

The microdrops of alginate containing the cells will be gelled (step 807) in a collection beaker containing containing, e.g., 1.2% $CaCl_2$ solution. The beads (microspheres) are first coated (step 809) with poly-L-ornithine at a first concentration, e.g., poly-L-ornithine 0.12%. The beads are then coated with poly-L-ornithine at a second concentration, e.g., poly-L-ornithine 0.06% (step 810).

The final degelling process is obtained by placing the microspheres in a solution of, e.g., 55 mM sodium citrate in saline for 4-5 minutes in manual oscillation (step 811). The volume of solution used is twice the volume of microspheres whose core must be de-gelled.

After this time, the microcapsules are subjected to successive coatings (e.g., two sequential coatings) of sodium alginate. For example, the first coating (step 813) is carried out with sodium alginate 0.1% for 10 minutes using, e.g., a volume of solution twice the volume of microcapsules to be coated in manual oscillation. The second coating (step 815) may be carried out using sodium alginate 0.05% in saline for 10 minutes in manual oscillation. The microcapsule are then washed (e.g., two rapid washes are performed) with saline solution and the microcapsules containing the cells are placed in complete culture medium (e.g., CMRL 10% Fetal Bovine Serum (FBS)) in an incubator 903 (step 817).

It is noted that other percentages, solutions, times and order of steps may be employed.

These changes included in the present method of microencapsulation induce the microencapsulated cells to form three-dimensional compact aggregates. In particular, in about 16-24 hours of incubation in culture medium in the incubator, the cells to form the cell aggregates become approximately spherical. Each microcapsule contains one or more cellular aggregates—large aggregates plus some small aggregates. The cells not included in these structures, which are present as single cells, are a fairly small percentage compared to the aggregate(s).

New Cellular Model: Myofibroblasts:

The myofibroblasts (e.g., isolated from Wharton's jelly of the human umbilical cord) also known as "human cord matrix-derived cells". These cells are very advantageous because they do not pose ethical problems or regulatory issues, since they are retrieved from the umbilical cord (not from umbilical cord blood) after childbirth, both spontaneous and caesarean section. And, as well known, this material usually is otherwise discarded. These cells express markers (CD10, CD13 CD29, CD44, CD90, CD117, SCF, etc.) that either make them close to the non-hematopoietic mesenchymal cells (Dominici 2006) or reflect an undifferentiated stem cells status (OCT4, SOX2, NANOG, Wnt, (Baksh 2007) (Weiss 2006, Carlin 2006). However, these cells differ from pure stem cells because they express markers of sternness but also pleiotropic markers that are typical of all three germ layers (RUNX2, PPAR, FABP4, osteopontin, Nestin, Vimentin, Islet1, Insulin, MafA, MafB, Tubulin betaIII, etc. . . . ), and finally, also of xtra-embryonic tissues. All this therefore raises the panel of markers in a state of stem cells that can be termed "single".

Myofibroblasts obtained from the Wharton Jelly can differentiate to multiple phenotypes (Montanucci 2011). It can give rise to extraembryonic mesoderm, adipocytes, chondrocytes, osteocytes, cardiomyocytes, skeletal muscle, liver and neural cells to mention the differentiation pathways that can be easily accomplished.

The myofibroblasts of the matrix of human umbilical cord have been associated, in vitro, with immunomodulatory properties, as shown by their ability to suppress the proliferation of lymphocytes and the formation of cytotoxic T cells and natural killer cells when present in mixed cultures of lymphocytes (Bartholomew 2002), to prolong indefinitely skin grafts, or to induce the differentiation of tolerogenic dendritic cells or to promote the expansion of CD25+Treg (Bartholomew 2002, Di Nicola 2002, Barry 2005). The mechanism through which the human umbilical cord matrix stem (hUCMS) cells are able to suppress lymphocyte proliferation is largely unknown but it seems, at least in part, mediated by soluble factors. In fact, various factors such as prostaglandin E2, IDO (indoleamine 2,3-dioxygenase-mediated tryptophan depletion) TGF-beta1 (Transforming Growth Factor-beta1) and HGF (hepatocyte growth factor) between the molecules are proposed to mediate the suppression, but experimental evidence remains conflicting (Inglese 2007, Xu 2007).

The myofibroblasts in the matrix of the umbilical cord used in accordance with the present principles are preferably isolated solely and uniquely by the method ("isolation means" 905) reported from our group in the following publication: Montanucci P., Basta G., T. Pescara, Flagpoles I., Di Giovanni M., Calafiore R. "*New simple and rapid method for purification of mesenchymal stem cells from the human umbilical cord Wharton's jelly*," Tissue Eng. Part A. 2011 Nov. 17 (21-22):2651-61, the disclosure of which is incorporated herein by reference. This new method allows us to obtain a number of cells initially isolated greater than previously reported in the literature and especially in significantly shorter time. However, other methods may be employed that provide these same advantages.

Figures 2A, 2B, 2C:
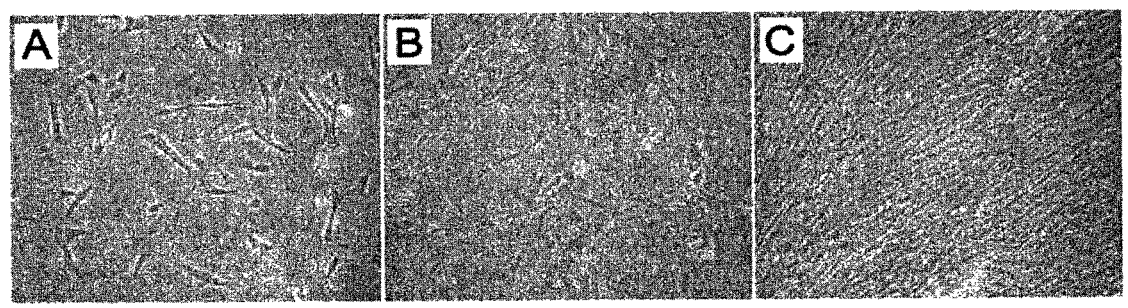
FIG. 2A shows exemplary myofibroblasts extracted from an umbilical cord matrix at 48 hours of isolation carried out according to an aspect of the present principles.
FIG. 2B shows exemplary myofibroblasts extracted from an umbilical cord matrix at 5 days of isolation carried out according to an aspect of the present principles.
FIG. 2C shows exemplary myofibroblasts extracted from an umbilical cord matrix at 7 days of isolation carried out according to an aspect of the present principles.

FIG. 2A shows exemplary myofibroblasts extracted from an umbilical cord matrix at 48 hours of isolation carried out according to an aspect of the present principles.

FIG. 2B shows exemplary myofibroblasts extracted from an umbilical cord matrix at 5 days of isolation carried out according to an aspect of the present principles.

FIG. 2C shows exemplary myofibroblasts extracted from an umbilical cord matrix at 7 days of isolation carried out according to an aspect of the present principles.

Figure 3A:
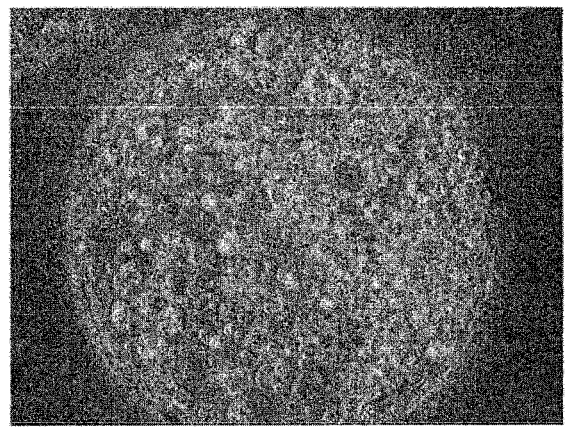
FIG. 3A shows exemplary myofibroblasts microencapsulated in sodium alginate, namely a phase contrast image of the microcapsules containing the hUCMS immediately after a procedure of encapsulation according to an aspect of the present principles.

FIG. 3A shows exemplary myofibroblasts microencapsulated in sodium alginate. Namely, FIG. 3A depicts an exemplary phase contrast image of the microcapsules containing the hUCMS immediately after a procedure of encapsulation according to an aspect of the present principles.

FIG. 3B shows exemplary myofibroblasts microencapsulated in sodium alginate, with staining of the cells with ethidium bromide and fluorescein diacetate for the estimation of the vitality. At this stage it is possible to estimate the viability to be over 95%.

FIGS. 4A, 4B and 4C depict exemplary myofibroblasts after 16 hours of a procedure of microencapsulation according to an aspect of the present principles. Already, after 16 hours of the procedure of microencapsulation, the microencapsulated myofibroblasts assumed a compact 3D architecture.

The assay shows how this vitality is not diminished compared to the evaluation carried out immediately after the procedure of microencapsulation.

Induction of Immunoregulation:

Myofibroblasts encapsulated in sodium alginate as described above were tested for immunoregulation ability of three different immunosuppressive autoimmune disorders: Sjogren's Syndrome, SLE, Type 1 Diabetes mellitus. The results obtained for all three diseases are superimposable. In all the three instances, a microcapsule/myofibroblast according to the present principles is able to suppress the proliferation of peripheral blood mononuclear cells taken from the patient and to transform the classes of T lymphocytes reactive regulatory T cells.

As an example, we report the data obtained using lymphocytes from patients with Sjogren's syndrome. Note that the results obtained are similar irrespective of the degree of disease presented by the subject (mild, medium or severe) but also from the phase of the disease in which it is located (phase of onset, intermediate stage or phase of clinical remission).

Figure 5:
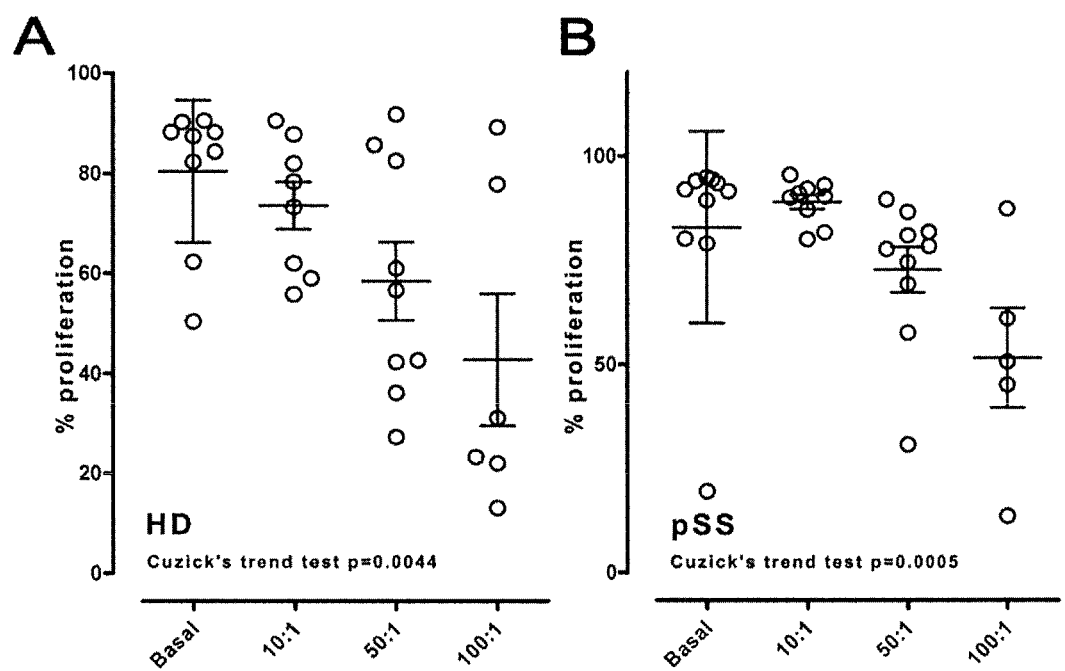
FIG. 5 is an exemplary set of graphs depicting a comparison in the reduction of the proliferation implemented by microencapsulated myofibroblasts against stimulated PBMC collected from a healthy subject (shown in Graph A) or from the subject with Sjogren's syndrome (shown in Graph B)

FIG. 5 is an exemplary set of graphs depicting a comparison in the reduction of the proliferation of stimulated PBMC collected from a healthy subject (shown in Graph A) or from the subject with Sjogren's syndrome (shown in Graph B), implemented by microencapsulated myofibroblasts according to an aspect of the present principles.

The extent of suppression is the same. Note the fact that with the decrease of the relative amount of myofibroblasts, the extent of immunosuppression becomes much more marked. Data was expressed as mean±SD in at last three independent experiments.

Figure 6:
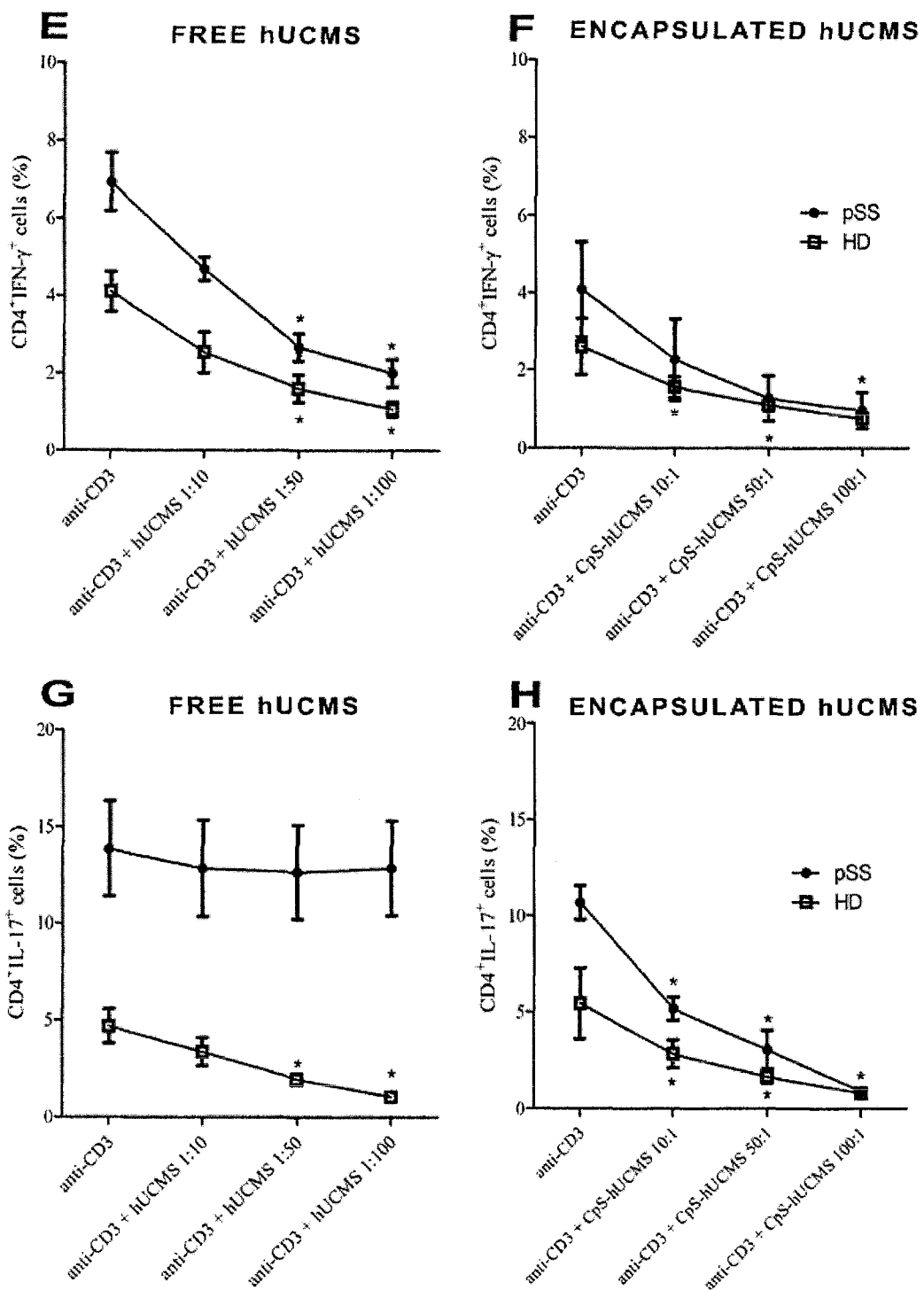
FIG. 6 is an exemplary set of graphs showing relationships between peripheral blood mononuclear cells Th1/Th17 performed by flow cytometry after co-culture of peripheral blood mononuclear cells from healthy donor (HD) or patients (pSS) with microencapsulated myofibroblasts.

FIG. 6 is an exemplary set of graphs (E, F, G, H) showing relationships between peripheral blood mononuclear cells Th1/Th17 performed by flow cytometry after co-culture of peripheral blood mononuclear cells from healthy donor (HD) or patients (pSS) with microencapsulated myofibroblasts.

As shown in FIG. 6, the Th1 lymphocytes from patients (pSS) and from healthy donors (HD) are inhibited by both free myofibroblasts from hUCMS (shown in Graph E) and microencapsulated myofibroblasts from hUCMS (shown in Graph F). As shown in Graphs G and H, the Th17 from healthy donors (HD) are inhibited by both free and microencapsulated myofibroblasts, while those from the patients (pSS) are only inhibited by microencapsulated myofibroblasts. Data are presented as means±SEM of three independent experiments. Asterisks: ($p<0.05$).

Figure 7:
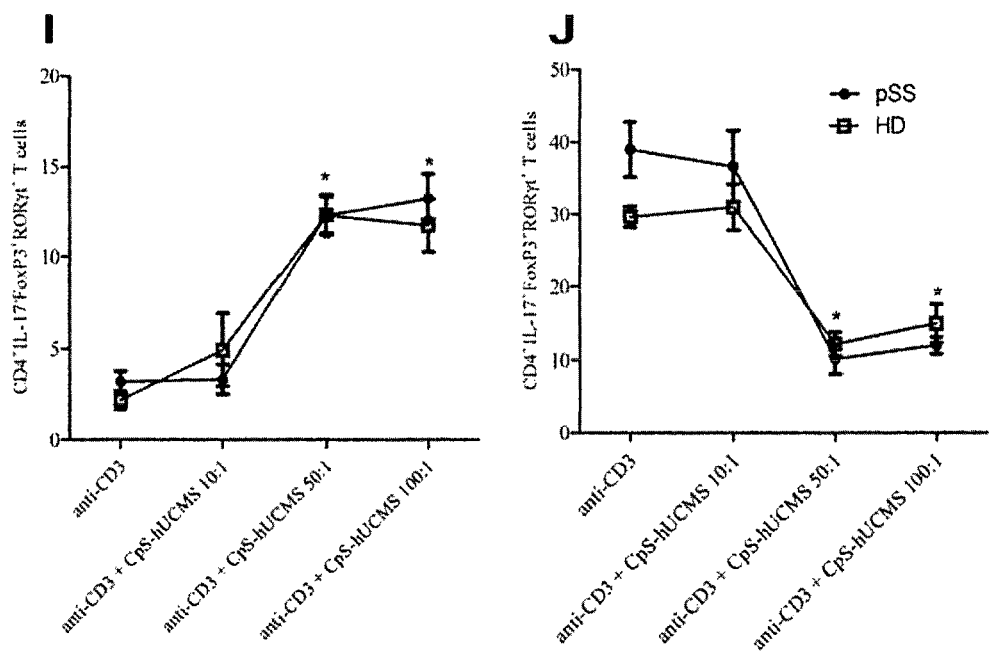
FIG. 7 shows an exemplary analysis of the expression of FoxP3 performed by flow cytometry.

FIG. 7 shows an exemplary analysis of the expression of FoxP3 performed by flow cytometry.

The expression of FoxP3 was determined in $CD4^+IL-17^-ROR\gamma t^-$ (I) and $CD4^+IL-17^+ROR\gamma t^+$ (J). The microencapsulated myofibroblasts modulate each other's expression of FoxP3 and RORγt. This indicates a conversion of Th17 cells in Treg cells.

Figure 9:
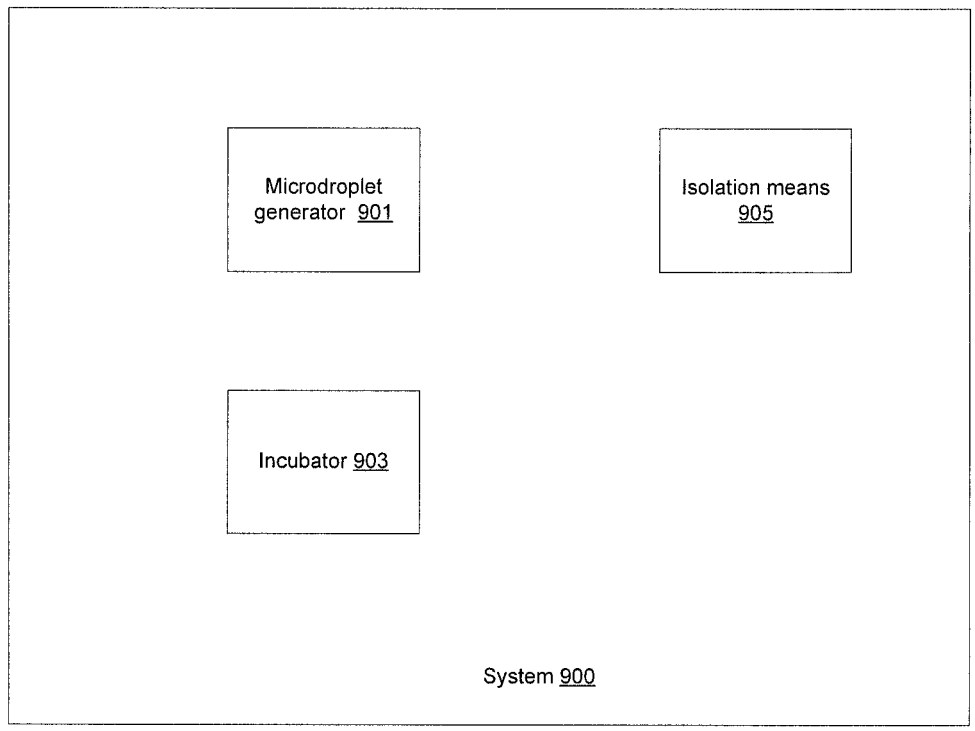
FIG. 9 depicts an exemplary system for microencapsulating cells using sodium alginate according to an aspect of the present principles.

FIG. 9 depicts an exemplary system 900 for microencapsulating cells using sodium alginate according to an aspect of the present principles, depicting a microdroplet generator 901, an incubator 903 and a cell isolation means 905.

Some Technical Features:

By using "clinical grade" Sodium Alginate produced, e.g., in accordance with the "Alginate disclosure," innovative features of procedures according to the present principles include wherein the process of microencapsulation, via a suitable procedure of degelling of the microcapsules' at the end of the production process, induces myofibroblasts in the microcapsules to take on a well-defined three-dimensional structure. The cell aggregates that are obtained are therefore of a spherical shape, compact and very viable. The omission of this degelling phase of degelling dramatically reduces cell viability and inability to perform immunoregulation. Such behavior has never been described in the microencapsulation of cells with immunoregulatory properties.

The tests carried out both with the microencapsulated or free myofibroblasts show that the experimental setting of co-culture with free myofibroblasts is not able to induce inhibition of proliferation of the lymphocytes from SSJ, or T1D, or SLE patients. However, microencapsulation of the isolated myofibroblasts advantageously results in immunomodulation of patients.

The purification process of myofibroblasts from the Wharton Jelly of the human umbilical cord may be based, e.g., on a method published in the international scientific journal "Tissue Engineering" by Montanucci P., Basta G., T. Pescara, Flagpoles I., Di Giovanni M., Calafiore R., "*New simple and rapid method for purification of mesenchymal stem cells from the human umbilical cord Wharton's jelly.*" Tissue Eng. Part A. 2011 Nov. 17 (21-22):2651-61. doi: 10.1089/ten.TEA.2010.0587. Epub 2011 Sep. 6, the disclosure of which is incorporated herein by reference.

Exemplary Application Fields:

The present principles have wide application in many fields and in many organs or tissue types. However, the present principles are particularly useful in the treatment of autoimmune diseases such as type 1 diabetes, Sjogren's syndrome, SLE, Hashimoto's thyroiditis, autoimmune diseases in general sharing predisposing gene haplotypes, etc.

Having described preferred embodiments for clinical grade sodium alginate for microencapsulation of myofibroblasts isolated from jelly Wharton human umbilical cord for prevention and treatment of autoimmune and inflammatory diseases (which are intended to be illustrative and not limiting), it is noted that modifications and variations can be made by persons skilled in the art in light of the above teachings. It is therefore to be understood that changes may be made in the particular embodiments of the invention disclosed which are within the scope of the invention as outlined by the appended claims. While the forgoing is directed to various embodiments of the present invention, other and further embodiments of the invention may be devised without departing from the basic scope thereof.

What is claimed is:

1. A method for microencapsulation of cells, comprising:
isolating myofibroblasts from Wharton's jelly of a human umbilical cord; and
microencapsulating the myofibroblasts using a solution of ultra-purified sodium alginate to form microcapsules comprising myofibroblasts encapsulated within sodium alginate, wherein the myofibroblasts encapsulated within the sodium alginate form a three-dimensional spherical structure, wherein the step of microencapsulating comprises:
mixing the myofibroblasts with the sodium alginate solution to form an alginate and cell suspension, and extruding the suspension through a microdroplet generator to form sodium alginate microdrops;
gelling the microdrops in a $CaCl_2$ solution to form microcapsules;
coating the microcapsules with poly-L-ornithine;
degelling the poly-L-ornithine coated microcapsules by placing the microcapsules in a solution of sodium citrate in saline in manual oscillation: and
after degelling, recoating the microcapsules with sodium alginate.

2. The method as recited in claim 1, wherein recoating includes successively recoating with layers of different concentrations of sodium alginate on the microcapsules.

3. The method as recited in claim 2, further comprising the step of incubating the microcapsules to induce the encapsulated myofibroblasts to form three-dimensional compact aggregates.

4. The method of claim 2, wherein the successive recoating comprises a first coating with sodium alginate 0.1% and a second coating with sodium alginate 0.05% in saline.

5. The method as recited in claim 1, further comprising delivering encapsulated myofibroblasts to a host to treat an autoimmune condition.

6. The method of claim 1, wherein the step of mixing comprises mixing the myofibroblasts with a 1.8% sodium alginate solution and wherein the alginate and cell suspension comprises 1.2 ml of 1.8% sodium alginate per $1$-$2 \times 10^6$ cells.

7. The method of claim 1, wherein the $CaCl_2$ solution comprises a 1.2% $CaCl_2$ solution.

8. The method of claim 1, wherein the step of coating the microcapsules with poly-L-ornithine comprises coating the microcapsules with poly-L-ornithine at a first concentration and coating the microcapsules with poly-L-ornithine at a second concentration.

9. A method for microencapsulation of cells, comprising:
isolating myofibroblasts from Wharton's jelly of a human umbilical cord; and
microencapsulating the myofibroblasts using a solution of ultra-purified sodium alginate to form microcapsules comprising myofibroblasts encapsulated within sodium alginate, wherein the myofibroblasts encapsulated within the sodium alginate form a three-dimensional spherical structure, wherein the step of microencapsulating includes:
mixing the myofibroblasts with the sodium alginate solution to form an alginate and cell suspension comprising 1.2 ml of 1.8% sodium alginate per $1$-$2 \times 10^6$ cells, and extruding the suspension through a microdroplet generator to form sodium alginate microdrops;
gelling the microdrops in a $CaCl_2$ solution to form microcapsules;
successively coating the microcapsules with different concentrations of poly-L-ornithine;
degelling the poly-L-ornithine coated microcapsules by placing the microcapsules in a solution of sodium citrate in saline in manual oscillation; and
after degelling, successively recoating the microcapsules with successive coatings of sodium alginate at different concentrations.

10. A pharmaceutical product made in accordance with claim 1.

* * * * *